United States Patent
Smith et al.

(10) Patent No.: US 7,025,828 B2
(45) Date of Patent: Apr. 11, 2006

(54) SCREENING FOR OPTIMAL YIELD IN THE CRYSTALLIZATION OF MULTICOMPONENT SYSTEMS

(75) Inventors: Alan Arthur Smith, Heemstede (NL); Lisa Lynn Agocs, Amsterdam (NL); Benjamin Mckay, Amsterdam (NL); Francois Gilardoni, Badhoevedorp (NL)

(73) Assignee: Avantium International B.V., Amsterdam (NL)

( * ) Notice: Subject to any disclaimer, the term of this patent is extended or adjusted under 35 U.S.C. 154(b) by 0 days.

(21) Appl. No.: 10/415,808

(22) PCT Filed: Nov. 5, 2001

(86) PCT No.: PCT/NL01/00803

§ 371 (c)(1), (2), (4) Date: Oct. 6, 2003

(87) PCT Pub. No.: WO02/36526

PCT Pub. Date: May 10, 2002

(65) Prior Publication Data

US 2004/0045498 A1    Mar. 11, 2004

(30) Foreign Application Priority Data

Nov. 6, 2000 (GB) .................................... 0027082
Jan. 29, 2001 (GB) .................................... 0102267

(51) Int. Cl.
*C30B 7/14* (2006.01)

(52) U.S. Cl. ............................. 117/68; 117/69; 117/70; 117/202; 422/245.1

(58) Field of Classification Search .................. 117/68, 117/69, 70, 202; 422/245.1, 249
See application file for complete search history.

(56) References Cited

FOREIGN PATENT DOCUMENTS

EP    0 553 539 A    8/1993

OTHER PUBLICATIONS

Smith, A.A., Calculation of the efficiency of purification by crystallization of ideal multicomponent stereoisomeric mixtures; Tetrahedron: Asymmetry, Elsevier Science Publishers, Amsterdam, NL; vol. 9, No. 16; Aug. 1, 1998 pp. 2925-2937.

*Primary Examiner*—Robert Kunemund
(74) *Attorney, Agent, or Firm*—Hoffmann & Baron, LLP

(57) ABSTRACT

A method of determining the optimal yield of a target compound includes the steps of:
(a) determining the initial composition of a mixture of compounds containing the target compound;
(b) dissolving the mixture in a solvent;
(c) placing a quantity of the solution in a plurality of vessels;
(d) optionally, placing a portion of a different derivatising agent in each vessel;
(e) causing crystallisation to occur;
(f) analysing the contents of the vessels after the crystallisation has approached equilibrium to determine the compositions of the liquors and the compositions of the solids; and
(g) comparing the compositions determined in step (f) to profile the performance of each system in terms of the projected maximum yield of target compound is an optimised crystallisation process.

12 Claims, 2 Drawing Sheets

SCREENING FOR OPTIMAL YIELD IN THE CRYSTALLIZATION OF MULTICOMPONENT SYSTEMS

FIELD OF THE INVENTION

The present invention relates to the purification of multicomponent mixtures. In particular, the present invention relates to the purification by crystallisation of such mixtures. More specifically, the present invention is concerned with a method of determining the optimal yield of a particular component from a multicomponent system which may be of assistance in determining a synthetic strategy or a programme of combinatorial synthesis.

BACKGROUND OF THE INVENTION

Chemical transformations, to a greater or lesser extent, result in a mixture of products and purification of the desired product is often achieved by crystallisation. Purification by crystallisation relies on preferential dissolution of a portion of the sample containing the unwanted components, along with a quantity of the desired component. The amount of desired component lost during this purification process is of particular importance in an industrial or commercial context and it would clearly be desirable to minimise the losses of desired components.

One example of a multicomponent mixture that is likely to require separation into its constituents is a stereoisomeric system involving chiral centres. In a stereoisomeric system, the number of possible stereoisomers for any given compound is $2^n$, where n is the number of asymmetric atomic centres. Thus, a system with two chiral centres provides four possible stereoisomers (notwithstanding the possibility of the optionally inactive meso form). Three chiral centres would give eight possible stereoisomers, and so on.

In many chemical reactions in which chirality is an issue, stereoisomeric purity is less than perfect. It may be that stereochemical corruption occurs during processing, that the selectivity of the process is less than optimal, or simply that the optical purity of the starting materials is low. In any case, the end result is that the products of the reaction are contaminated with unwanted stereoisomers.

Historically, removal of the unwanted stereoisomers has been achieved by crystallisation and, although modern techniques such as Simulated Moving Bed Chromatography are gaining acceptance, it is likely that crystallisation will remain the dominant method of purification for the foreseeable future.

In view of the foregoing and the fact that the historical approach relied on a series of "trial and error" experiments, and particularly because of the demand of the pharmaceutical industry for chiral products of high stereochemical purity coupled with the increase in the number of chiral pharmaceutical agents, a method for calculating the maximum yield from a multicomponent mixture of stereoisomers was developed. This method is described in Tetrahedron: Asymmetry 9 (1998), 2925–2937. Of course the demands of the pharmaceutical industry in this regard are also becoming increasingly important in other technical areas, such as the fine chemical, agrochemical and electronics markets.

The approach is based on, but not restricted to, the Ideal approximation. For optimal recovery, it is necessary to dissolve no more of the sample than the maximum amount of material in the sample having a composition corresponding to the eutectic. Therefore, the basis of estimating the maximum recovery of pure component from the mixture by crystallisation requires knowledge of the composition of the eutectic. In the first instance, it is assumed that the eutectic is not influenced to an appreciable degree by the solvent. It is reckoned that this is a reasonable approximation in the case of stereoisomers, since these have the same functionality arranged on a very similar skeleton, so differences in influences of the solvent between the isomers will be minimal.

In the first instance, it is also assumed that the system behaves as a conglomerate, as described by the Shroeder-Van Laar equation. A conglomerate is a mechanical mixture of enantiomeric crystals which are resolvable by entrainment or triage.

In the non-ideal case, if more than one isomer type crystallises in the unit cell, for example in the case of a racemic compound, the Prigogine-Defay equation can be applied. Determination of the optimal yield based on this approach requires the following information:
- the melting point of each component;
- the heat of fusion of each component;
- determination of conglomerate or racemic compound behaviour, and
- the initial composition of the mixture.

These may then be derivatised, for example as salts, esters or the like, depending on the molecular functionality. Their melting points and heats of fusion are subsequently determined, using differential scanning calorimetry (DSC) followed by calculation of the maximum theoretical yield. Although this process can be simplified using automated systems, it still represents a significant up-front overhead of:
- isomer separation;
- preparation of derivatives of each isomer;
- determination of the nature of the crystal form—are they conglomerates or racemic compounds?

Whilst this approach, for the first time, provided the basis for a rational evaluation of the purification process in multicomponent systems, it suffers from the limitation of requiring separation of the stereoisomers.

Moreover, there are inherent limitations due to the possibility of thermal instability of the materials, making DSC analysis unreliable. Additionally, the fact that the derivatives are prepared separately may introduce the possibility of polymorph formation which would not otherwise occur in crystallisation of the mixture. This can lead to errors in subsequent measurements and calculation.

It is therefore an object of the present invention to provide a means for determining the optimal yield for obtaining a purified product from a multicomponent system that avoids the above problems.

SUMMARY OF THE INVENTION

The invention is a method of determining the optimal yield of a target compound isolatable from a mixture of compounds, the method comprising the steps of:
(a) determining the initial composition of a mixture of compounds containing the target compound;
(b) preparing a plurality of different solutions in a plurality of vessels, comprising the steps of
  (b1) placing the mixture in the plurality of vessels;
  (b2) placing one or more solvents in the plurality of vessels, steps b1 and b2 forming a plurality of solutions in the said vessels;
  (b3) optionally, placing a portion of a different derivatising agent in each vessel;
(c) causing crystallisation to occur;

(d) analysing the contents of the vessels after the crystallisation has approached equilibrium to determine the compositions of the liquors and the compositions of the solids; and (e) comparing the compositions determined in step (d) to profile the performance of each system (by calculated means) in terms of the projected maximum yield of target compound in an optimised crystallisation process.

The person skilled in the art will understand that in step (b) the mixture may be dissolved in one or more solvents to form a number of solutions and this may involve formation of a derivative (e.g. a salt).

Optionally, the step (d) of analysing the contents of the vessels after the derivatising reactions reach equilibrium may involve the removal of the original solvent system, for example evaporatively, followed by equilibration of the mixture using an alternative solvent. Then the compositions of the liquors and the compositions of the solids are determined.

The measurements carried out in step (d) may be used in combination with information provided by calculational means to structure a series of subsequent experiments with the aim of rapidly optimising the yield of the purification process.

It will be understood by persons skilled in the art that steps (a) to (e) outlined above do not necessarily have to be carried out in the listed order provided that the overall effect of the method is the same. For example, it is equivalent to place different derivatising agents in the plurality of vessels and then add portions to each vessel of the solution of the mixture of compounds. In addition, it will be understood by persons skilled in the art that the invention also includes minor modifications to steps (a) to (e) provided that the effect of the method is substantially the same. For example, evaporating the solvent after step (c) to isolate the solid and re-dissolving it in a specified amount of another solvent prior to inducing e.g. crystallisations.

The method outlined above lends itself to high throughput screening using an automated system for spatially addressed delivery of reagent, substrate and solvent to an array of vessels. The method is especially suitable for dealing with small quantities of mixtures and a large number of derivatisation conditions. Given the large numbers of solutions to be prepared, the method preferably includes a temporally efficient procedure for determining an appropriate range of solvent volumes to be dispensed to each vessel. For example, this could be done by adding incremental volumes of solvent to a vessel containing the derivatised mixture, determining the composition after each addition step and calculating an appropriate range of volumes for subsequent experimentation. Because the analysing step to determine the compositions of the liquors and the compositions of the solids requires only small quantities of material (using techniques such as gas chromatography, capillary electrophoresis, high performance liquid chromatography, coupled with the ability to extract detailed physical characteristics of the system by calculational means) the method of the present invention represents a significant technical advance over prior art methods. Such prior art methods may rely on:

(1) A laborious experimental programme, based on a linear sequence of process optimisation experiments (i.e. the classical experimental approach). This is very difficult to achieve on small quantities of materials and is also time-consuming;

(2) Separation of each component of the mixture, (optionally derivatisation of each isolated compound) and subsequent determination of their melting points, heats of fusion, and phase diagram relationship (conglomerate or racemic compound).

By contrast, the method of the present invention does not require this initial isolation step, nor does it require the determination of melting points and heats of fusion, which is a significant advance considering potential loss of data where thermal instability is a problem. Importantly, since the current method makes use of measurement of the actual solubility behaviour of the components in the presence of a solvent, deviations from Ideality are absorbed into the invention to some extent, whereas the original model described in the Tetrahedron Asymmetry paper was limited to the Ideal approximation. In the non-ideal case (if the eutectic composition is influenced to an appreciable degree by the solvent), the effect of solvent can be inferred by comparing results obtained using different solvents. Once solvents have been characterised using suitable descriptors, statistical experimental design techniques can be used to facilitate an efficient selection of solvents for subsequent experimentation. Empirical modelling methods (e.g linear regression) can be used to quantify the relationship between the solvent descriptors and the observed solvent effects. This relationship can then be used to optimise solvent choice by screening a virtual library of solvents. Therefore the current method provides more accurate results. Moreover, it is well suited to highly parallel procedures and automated systems and is thus temporally efficient.

The method preferably includes deconvoluting the composition data from the initial mixture and the partially purified material to calculate the final yield.

For example, this can be done by measuring the rate of change of each component using different volumes of solvent for a given derivatisation reaction; an optimisation algorithm can be used to establish a yield prediction using the initial, crystallised, and liquor composition data from one or more volumes of solvent. Alternatively, an empirical model (e.g. neural network), once trained, can be used for yield prediction using only the initial composition, the crystallised composition data, and the liquor composition data from crystallisations performed using one or more volumes of solvent.

The maximum yield of target compound can then be determined. It is also possible to calculate the compositions of solids and liquors at any arbitrary point during a purification process. Moreover, at this point it is immediately possible to calculate the volume of solvent required to achieve maximal recovery of the target compound. Using this technique, it is possible to prioritize selection of systems from the initial study for further investigation and optimisation. In addition, given estimates of the precision of the composition measurements, a measure of the confidence in the predicted yield of target compound (or the predicted solid and liquid compositions at arbitrary points during a purification process) can be calculated, providing further guidance in the planning of additional experiments.

In a second aspect, the invention is an apparatus for determining the optimal yield of a target compound to be isolated from a mixture-of compounds, the apparatus comprising:

(a) a plurality of vessels;

(b) means for apportioning a solution of the mixture of compounds between the plurality of vessels;

(b1) means for evaporating solvent;

(b2) means for dispensing different solvents to each vessel;

(c) means for adding a portion of a different derivatising agent to each vessel;

(d) analysing means for determining the compositions of the liquors and the compositions of the solids in each vessel; and (e) comparator means for comparing the compositions determined by the analysing means (d) to determine which systems provide the best yield of target compound.

Preferably the apparatus comprises means for evaporation of solvent and dispensing different solvents.

Preferably, the apparatus includes computer control systems for automatically dispensing solids and liquids, regulating the crystallisation conditions, taking samples and analysing compositions. For example, automated control of cooling profiles could be achieved by on-line monitoring of turbidity and composition by means of spectroscopic techniques. In addition, the apparatus would preferably include a means for determining when a system is approaching thermodynamic equilibrium. Preferably, the apparatus includes a data storage device with software for storing and retrieving experimental results. Preferably, the apparatus comprises means for inducing crystallisation. This may or may not involve the use of specific apparatus; for example, crystallisation may occur spontaneously following reaction with a derivatising agent, or be induced by a cooling apparatus.

Preferably, the apparatus includes means to define a subsequent series of experiments on a selection from an initial experimental array for the purpose of confirming the optimum yield of target compound.

Further, the apparatus preferably includes a means for automatically determining the precision and accuracy with which step (a) to (f), outlined above, have been carried out. Preferably the apparatus further includes software for calculating the impact of this experimental error on the predicted optimal yield (or the predicted solid and liquid compositions at an arbitrary recovery).

Preferably, the apparatus further includes a computer program to calculate all necessary parameters such as predicted maximum yield and solubility of the eutectic in each case.

Preferably, the apparatus includes computer software to allow an operator to visualise the operational status and interactively control the apparatus. In addition, the apparatus will preferably include software for the display of predicted yield and other information.

BRIEF DESCRIPTION OF THE DRAWING

The invention will now be described by way of example only with reference to the drawings, in which.

BRIEF DESCRIPTION OF THE INVENTION

Figure 1:
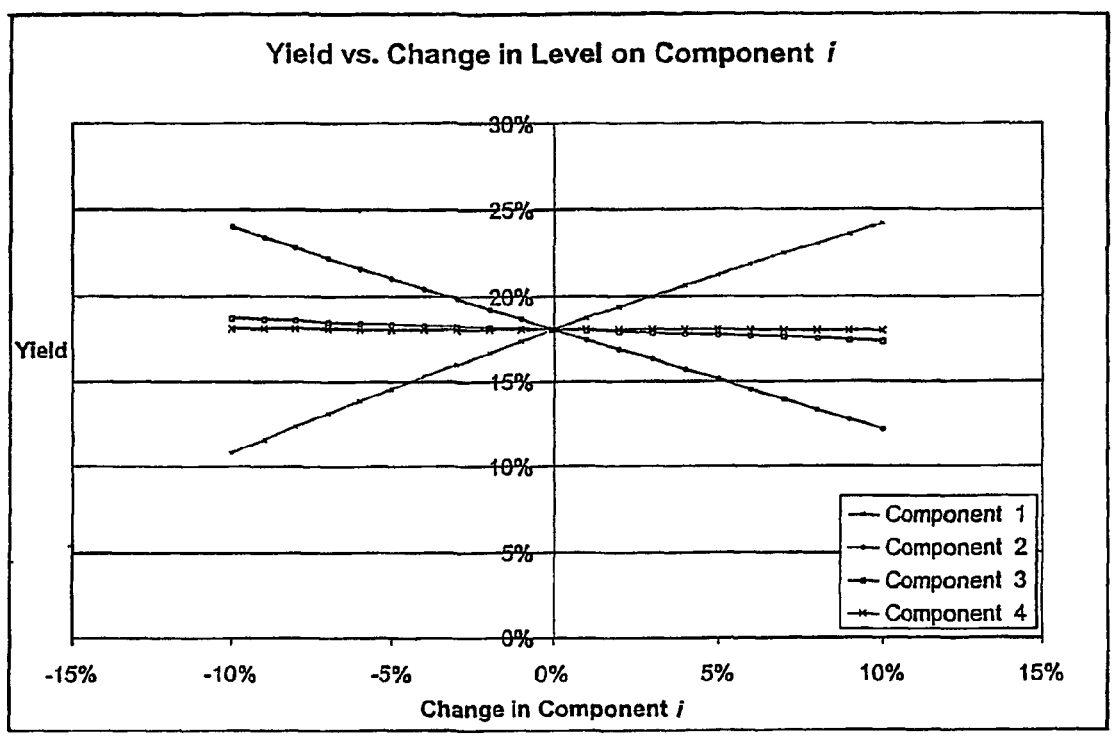
FIG. 1 is a graph showing the yield sensitivity of a multicomponent mixture to changes in the proportions of each of its components.

Referring firstly to FIG. 1, consider a mixture of four stereoisomers comprised in a mixture in the following proportions: 81%, 9%, 9% and 1%. Components 2 and 3 are present in the same proportions, but this does not necessarily mean that a 1% reduction in proportion will have the same effect in both cases.

It is noted that the effect on yield is at least locally linear. This is an illustration of the ideal behaviour of the system. Negative gradients are associated with the minor components, which may be regarded as the impurities. Lower recovery of pure isomer will result as the proportion of the minor components increases. Changes in component 2 dominate the change in yield of the process. Even though components 2 an 3 are present in equal proportions in the initial mixture, it is clear from FIG. 1 that changes in the proportion of component 2 will be more influential on the yield of the target compound (component 1) than changes in the proportion of component 3.

Figure 2:
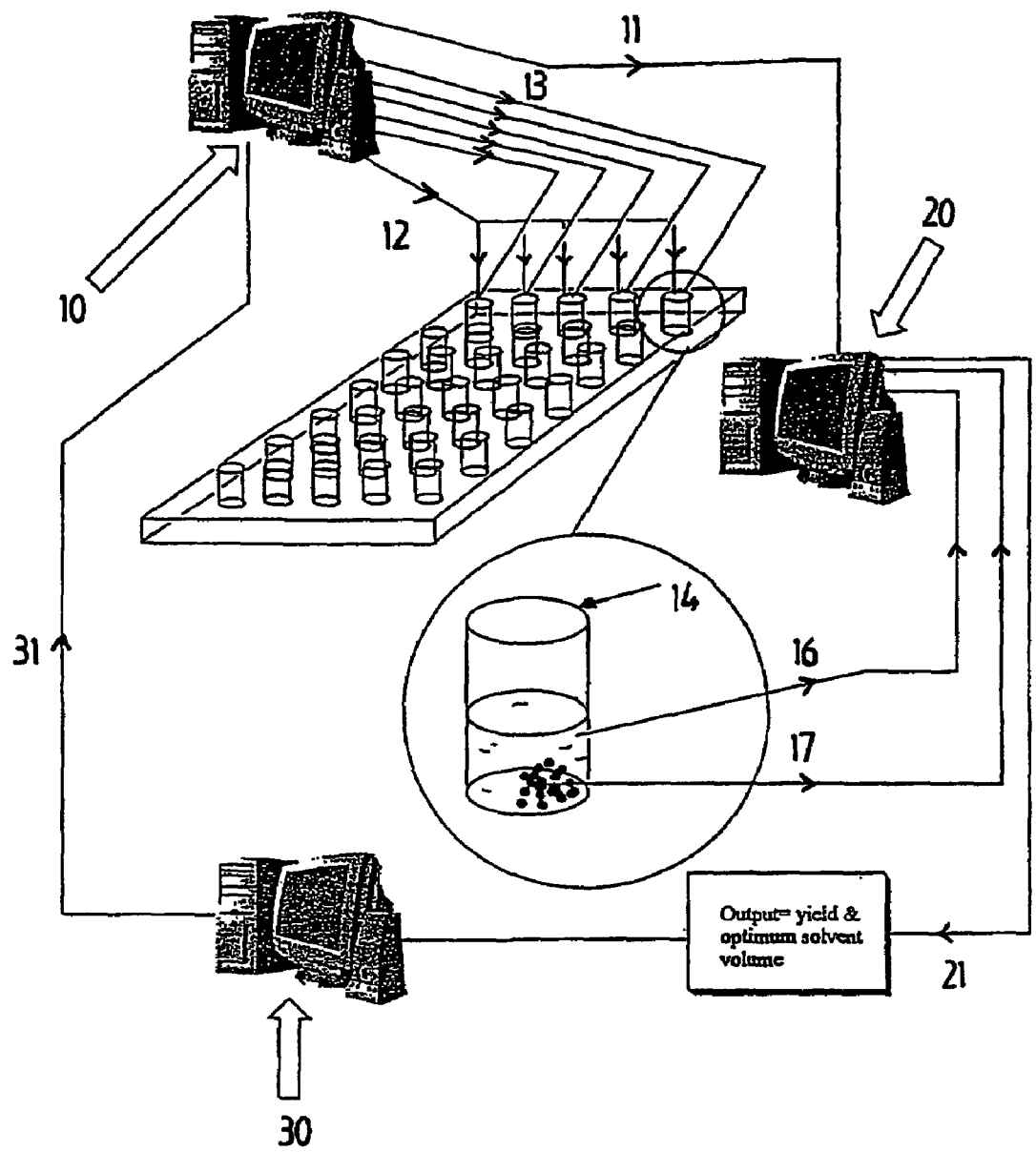
FIG. 2 is a schematic view of a system embracing the present invention.

FIG. 2 is a schematic view of an example system for carrying out the method of the present invention. Reference numeral 10 denotes a computer controlled automated delivery system, reference numeral 20 denotes a computer controlled sampling and analysis system and reference numeral 30 denotes a computer controlled system for prioritising results obtained from computer controlled sampling and analysing system 20.

Computer controlled automated delivery system 10 controls the delivery to an array of reaction vessels 14 of a predetermined quantity of a mixture 12 containing the target compound. The automated delivery system 10 also controls the delivery to each of the reaction vessels 14 of a quantity of a different derivatising agent 13. The portions of the mixture 12 and the different derivatising agents 13 are caused to react together with the aim of derivatising the components of the mixture 12. The mixture is allowed to equilibrate between a liquid phase and a solid, crystalline phase.

A temperature regulation apparatus 41 controlled by a process control system 40 regulates the reaction and crystallisation conditions until thermodynamic equilibrium is approached.

Initial composition data 11 is sent from the automatic delivery system to the computer controlled sampling and analysis system 20. The sampling and analysis system 20 samples the mother liquors 16 from each reaction vessel 14 and analyses the composition of the mother liquors to determine the proportion of each component of the mixture present. A mass balance is conducted to determine the relative proportions of the constituents in the solid phase.

The compositional information 21 obtained by the sampling and analysis system 20 is passed to the computer controlled prioritisation system 30, where the information is analysed to prioritise which of the systems merit further study. The prioritisation system may be used to design and conduct experiments based around the calculated optimum solvent volume. The output 31 of the prioritisation system is a set of instructions to the computer controlled automated delivery system 10 for conducting a further round of experiments.

Although the invention has been particularly described above with reference to examples, it will be understood by persons skilled in the art that variations and modifications are possible without departing from the scope of the claims which follow.

What is claimed is:

1. A method of determining the optimal yield of a target compound isolatable from a mixture of compounds, the method comprising the steps of:

(a) determining the initial composition of a mixture of compounds containing the target compound;

(b) preparing a plurality of different solutions in a plurality of vessels, comprising the steps of (b1) placing the mixture in the plurality of vessels;

(b2) placing one or more solvents in the plurality of vessels, steps b1 and b2 forming a plurality of solutions in the said vessels;

(b3) optionally, placing a portion of a different derivatising agent in each vessel;

(c) causing crystallisation to occur;

(d) analysing the contents of the vessels after the crystallisation has approached equilibrium to determine the compositions of the liquors and the compositions of the solids; and (e) establishing a yield prediction by using an optimization algorithm using the composition data from the mixture of step (a) and the composition data of step (d) from one or more volumes of solvent, wherein the method is based on the ideal approximation and uses the measurement of the actual solubility behavior of the compounds in the presence of the solvent.

2. A method as claimed in claim 1 wherein step (e) further comprises profiling the performance of each derivatising agent in terms of the projected maximum yield of target compound in an optimised crystallisation process.

3. A method as claimed in claim 1 or claim 2 comprising measuring the rate of change of each component using different volumes of solvent for at least one of the derivatisation reactions.

4. A method as claimed in claim 1 further comprising the step of calculating the solubility of an eutectic for determining the volume of solvent necessary for optimal recovery.

5. A method as claimed in claim 4 wherein a subsequent series of experiments is defined on a selection from the initial experimental array.

6. A method as claimed in claim 1 wherein the step (c) is followed by the removal of the original solvent, followed by equilibration of the mixture using an alternative solvent.

7. An apparatus for determining the optimal yield of a target compound to be isolated from the mixture of compounds, the apparatus comprising:

(a) a plurality of vessels;

(b) means for apportioning a solution of the mixture of compounds between the plurality of vessels;

(b1) means for evaporating solvent;

(b2) means for dispensing different solvents to each vessel;

(c) means for adding a portion of a different derivatising agent to each vessel;

(d) analysing means for determining the compositions of the liquors and the compositions of the solids in each vessel; and (e) optimization means for establishing a yield prediction by using an optimization algorithm using the composition data from the mixture of compounds and the composition data from the analysing means of (d) from one or more volumes of solvent, wherein the optimization means is based on ideal approximation and the measurement of the actual solubility behavior of the compounds in the presence of the solvent.

8. Apparatus as claimed in claim 7 further comprising means for determining solubility of the eutectic in each reaction vessel.

9. Apparatus as claimed in claim 7 further comprising means for controlling automated delivery of solids, liquids and solutions to the plurality of vessels.

10. Apparatus as claimed in claim 9 further comprising means for controlling automated sampling on the initial composition, and the solid and liquor compositions of each vessel.

11. Apparatus as claimed in claim 9 further comprising a computer-controlled analytical system.

12. Apparatus as claimed in claim 7 including a computer programmed to calculate the final yield of target compound and the solubility of the eutectic.

* * * * *